United States Patent [19]

Nosé et al.

[11] Patent Number: 4,619,639
[45] Date of Patent: Oct. 28, 1986

[54] METHOD AND APPARATUS FOR LOW PRESSURE FILTRATION OF PLASMA FROM BLOOD

[75] Inventors: Yukihiko Nosé, Cleveland Heights; Paul S. Malchesky, Painesville Township, Lake County, both of Ohio

[73] Assignee: Asahi Medical Co., Ltd., Tokyo, Japan

[21] Appl. No.: 775,097

[22] Filed: Sep. 11, 1985

Related U.S. Application Data

[63] Continuation of Ser. No. 417,914, Sep. 14, 1982, abandoned, which is a continuation of Ser. No. 179,224, Aug. 18, 1980, Pat. No. 4,381,775, which is a continuation-in-part of Ser. No. 118,677, Feb. 5, 1980, abandoned.

[51] Int. Cl.$^4$ .............................................. A61M 1/03
[52] U.S. Cl. ........................................ 604/6; 604/4; 604/5; 210/927; 210/929; 210/433.2; 210/651
[58] Field of Search ....................................... 604/4–6; 210/927, 929, 406, 433.2, 651

[56] References Cited

U.S. PATENT DOCUMENTS 3,579,441 2/1971 Brown ................................. 210/23
3,705,100 12/1972 Blatt et al. ........................... 210/23
4,191,182 3/1980 Popovich et al. ..................... 604/6

FOREIGN PATENT DOCUMENTS

WO79/01121 12/1979 PCT Int'l Appl. .................... 604/6

OTHER PUBLICATIONS

K. Oachi et al.—"An Efficient, Specific and Blood Compatible Sorbent System for Hepatic Assist.", vol. XXIV, Trans. Am. Soc. Artif. Intern. Organs, 1978—Sep. 1978, pp. 246–248.

Primary Examiner—Richard J. Apley
Assistant Examiner—Gregory Beaucage
Attorney, Agent, or Firm—Wenderoth, Lind & Ponack

[57] ABSTRACT

A method and apparatus for carrying out separation of plasma from whole blood, in which whole blood is passed through a filtration membrane means of a material suitable for separating plasma from whole blood and having a pore size from 0.1 to 0.6 microns at positive pressure differential across the membrane in a range up to just below 50 mm Hg. This provides an increased flow as compared to the flow obtained with higher pressures.

10 Claims, 2 Drawing Figures

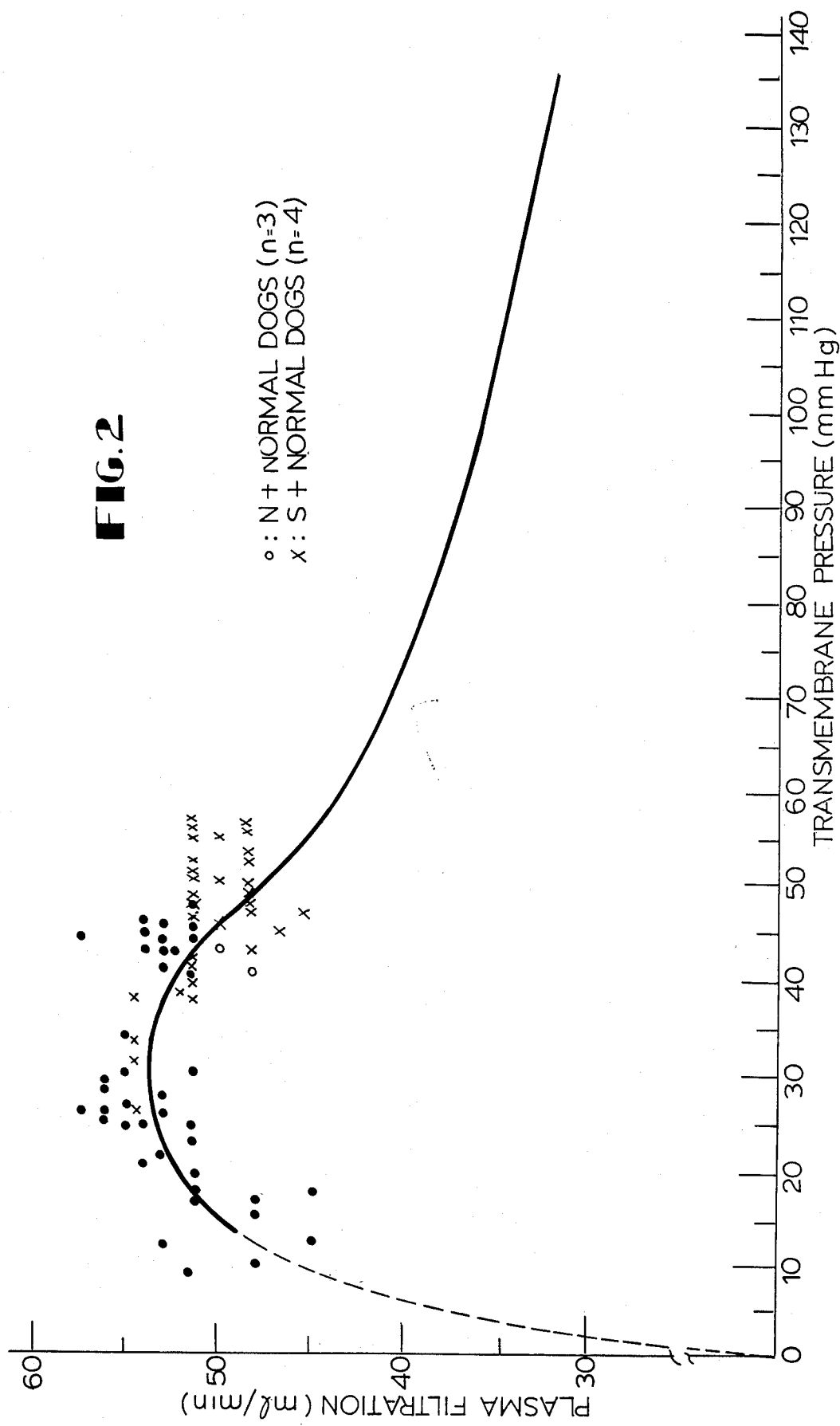

METHOD AND APPARATUS FOR LOW PRESSURE FILTRATION OF PLASMA FROM BLOOD

This application is a continuation of application Ser. No. 417,914, filed Sept. 14, 1982, now abandoned, which in turn is a continuation of application Ser. No. 179,224, filed Aug. 18, 1980, now U.S. Pat. No. 4,381,775, and is in turn a continuation-in-part of application Ser. No. 118,677, filed Feb. 5, 1980, now abandoned.

This invention relates to a method and apparatus for separating blood plasma from whole blood, i.e. blood from a person or animal, and more particularly to such a method and apparatus which operates at a relatively low pressure and yet obtains an improved quantity of separated plasma.

BACKGROUND OF THE INVENTION AND PRIOR ART

Until relatively recently, the separation of plasma from whole blood, such as for the purpose of utilizing the plasma from a donor for transfusion to others or for some sort of treatment of the blood, has been carried out by extracting the whole blood and centrifuging it to separate the plasma. Such procedures are not only time consuming and cumbersome requiring large amounts of manual and mechanical handling, but they require a relatively large amount of expensive equipment.

Recently investigations have been conducted into so-called on-line membrane plasma separation techniques. In this type of separation, the blood is passed through the on-line separation equipment and immediately returned to the donor, the plasma being separated and, in the case of a donor, collected and stored, or alternatively in a case of a patient, treated, such as by sorption of a solute which it is desired to remove, and then returned to the patient. In addition to being much simpler than the centrifugal techniques of plasma separation in terms of the manual and mechanical handling of the blood, and lower expense, this technique when used for the treatment of the plasma has advantages over the conventional treatment of solute removal which incorporate treating agents in direct contact with whole blood in that in many instances the solute which it is desired to remove is concentrated in the plasma, making the technique a rapid and simple way to cleanse the blood. The most suitable treatment material can be chosen and used for the particular treatment desired without the need to consider the effect of the treatment material on the blood cells, since blood cell-treating agent interaction are eliminated, multiple types of treating agents may be employed, and it is easy to filter the treatment material from the plasma before reinfusing it into the patient, thus providing a treatment methodology that is safe in a wide variety of applications.

One method of carrying out such a plasma separation technique and an apparatus therefor are disclosed in U.S. Pat. No. 3,705,100 to Blatt, et al. A membrane arrangement is shown in which the pore sizes are 0.1 to 0.8 microns, and the blood is passed over the surface of the membrane at a flow rate of 2-50 feet per minute while a pressure differential across the membrane is maintained at from 1 to 15 psi. This method and apparatus are said to be effective in separating the plasma from the whole blood.

A similar method is disclosed in K. Ouchi et al, An Efficient, Specific and Blood Compatible Sorbent System for Hepatic Assist, Vol. XXIV Transactions American Society Artificial Internal Organs 246, 1978, in which a cellulous acetate filter was used to separate plasma from whole blood flowing through the hollow fiber membranes at a rate of 100 ml/min. and at pressure differentials across the membrane of 60,100 and 137 mm Hg., the separation at these pressures being $37\pm2$ ml/min., $34\pm2$ ml/min. and $32\pm2$ ml/min. respectively.

Recently issued U.S. Pat. No. 4,191,182 to Popovich et al also discloses a method and apparatus for continuous separation of plasma by so-called ultra-filtering. As with the above-described prior art, Popovich et al also operate at transmembrane pressures in the 50-700 mm Hg. range. While recognizing that transmembrane pressures which are too high will cause damage to the cellular components of the blood and that control of transmembrane pressure is necessary to avoid clogging of the filter, Popovich et al nevertheless prefer to operate in the 100-400 mm Hg. range of transmembrane pressures.

OBJECTS AND BRIEF SUMMARY OF THE INVENTION

It is an object of the present invention to provide a method of separating blood plasma from whole blood, i.e. blood from a healthy and/or diseased person or animal, which method is even more efficient than the prior art method, yet which operates at a lower transmembrane pressure than the prior art methods so as to avoid problems of damage to cellular components of the plasma and clogging of the filter.

It is a further object of the invention to provide an apparatus for carrying out this method.

According to the present invention, it has been found that, contrary to normal expectations, by operating at a positive transmembrane pressure differential up to just below 50 mm Hg., and particularly from about 8.5 mm Hg. up to just below 50 mm Hg., the filtration rate of the plasma can be increased, as compared with filtration rates when operating above 50 mm Hg. The objects of the invention are thus achieved by directing a flow of whole blood across one face of filtration membrane means which is made of a material suitable for separating plasma from whole blood and having a pore size from 0.1 to 0.6 microns, said flow being at a flow velocity of from 5 to 1500 $^{cm}$/min and being at a depth sufficient for separating plasma from the flow of blood, while at the same time generating a positive pressure differential across said membrane up to just below 50 mm Hg., and particularly from about 8.5 mm Hg. up to just below 50 mm Hg., for forcing plasma through the membrane, and collecting the plasma separated by the membrane. Preferably the pressure is in a range of from about 40 to about 20 mm Hg.

This is different from conventional ultrafiltration, in which it is generally considered that the filtration rate increases with an increase in transmembrane pressure. The present invention demonstrates that the usual considerations do not apply in filtration of plasma from whole blood, possibly due to the complex mixture of particles in blood.

It has also been discovered that there is a further advantage in the plasma separation when it is carried out at such low transmembrane pressures. Plasma is an extremely complex fluid containing many solutes the molecules of which have different sizes. Current developments in the plasma filtering art are judged not only by the quantity of plasma which can be filtered, but by the quality or composition of the filtrate, one measure of which is sieving coefficient, namely the relative amounts of desired components of the plasma present in the filtrate as compared to the amounts of such components present in the blood from which the plasma is filtered. The present inventors have found that not only is the quantity of plasma which can be filtered from whole blood increased by operating at the low positive transmembrane pressures, but also the sieving coefficient for the various components of the plasma in increased.

The apparatus according to the invention for carrying out separation of plasma from whole blood comprises a filtration membrane means of a material suitable for separating plasma from whole blood and having a pore size from 0.1 to 0.6 microns; means for directing a flow of whole blood across one face of said membrane at a flow velocity of from 5 to 1500$^{cm}$/min and at a depth sufficient for enabling separation of plasma from the flow of blood; means for generating a positive differential across said membrane up to just below 50 mm Hg., and particularly from about 8.5 mm Hg. up to just below 50 mm Hg., for forcing the plasma through the membrane; and means for collecting the plasma separated by the membrane. The membrane means can be a film type membrane or a hollow fiber membrane for example, of cellulose acetate.

BRIEF DESCRIPTION OF THE DRAWINGS

Other and further objects of the invention will become apparent from the following detailed description, taken with the accompanying drawing, in which:

FIG. 2 is a graph of transmembrane pressure vs. plasma filtration rate according to the method of the present invention.

DETAILED DESCRIPTION OF THE INVENTION

Figure 1:
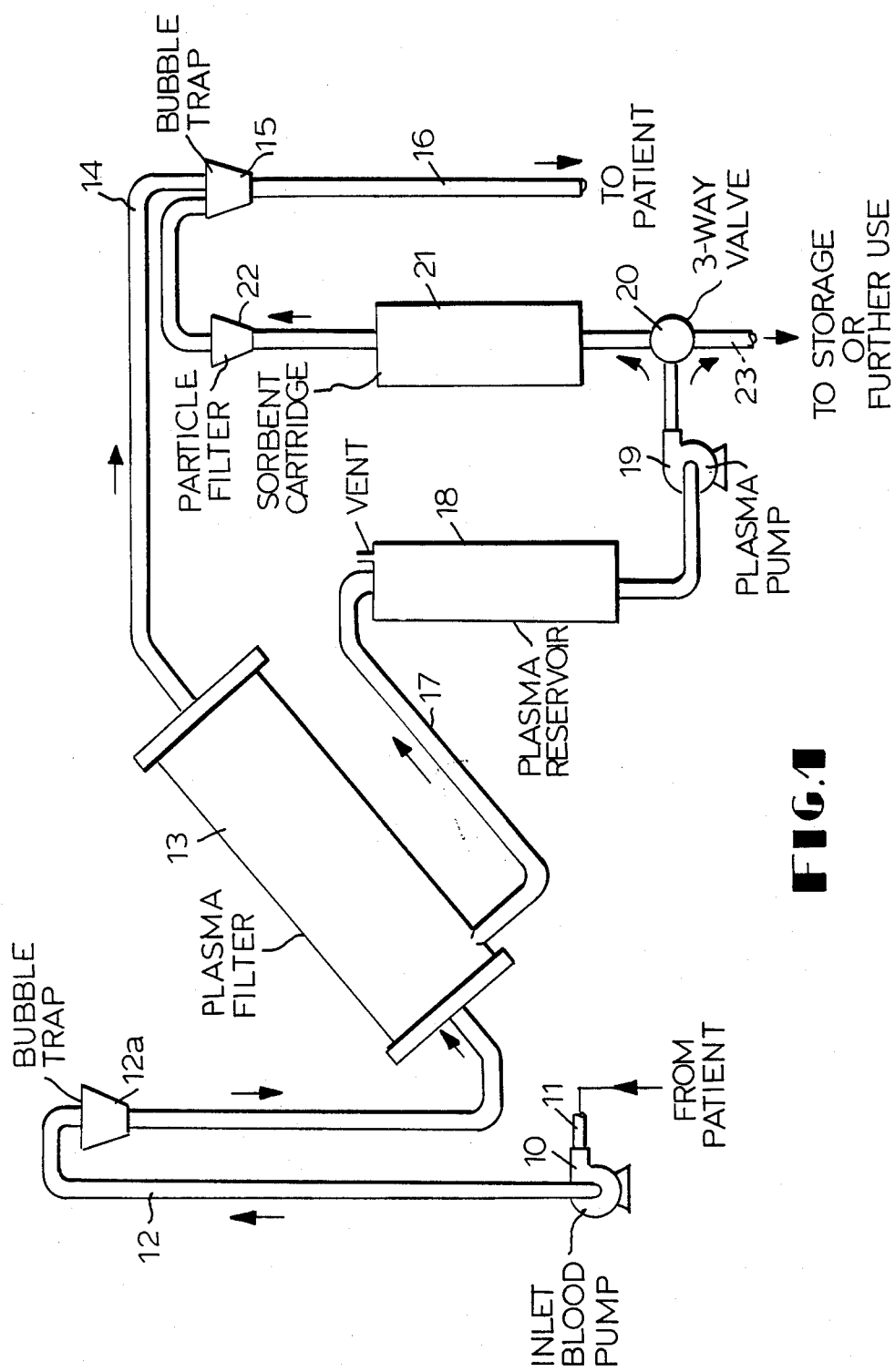
FIG. 1 is a schematic diagram of an apparatus for separating blood plasma from whole blood, collecting it, and then either treating it, and returning it to the patient after proper filtering, or forwarding it to storage or further use.

FIG. 1 shows schematically an apparatus for carrying out the method of the invention. The apparatus comprises an inlet blood pump 10 to the inlet of which a line or tube 11 from a patient or donor is connected and which has a tube 12 extending from the outlet thereof through a bubble trap 12a to the inlet to the whole blood face of a plasma filter 13. From the downstream end of the plasma filter 12 a further line 14 extends to a bubble trap 15 and a line 16 extends from the bubble trap back to the patient. From the filtrate face of the filter 13 a line 17 extends to a plasma reservoir 18 and the conduit means continues in the form of a line extending from the outlet of the plasma reservoir connected to a plasma pump 19 the outlet of which is in turn connected to a three-way valve 20. Extending from one outlet to the valve 20 is a line 23 leading to collection means or the like for collecting the plasma for further use, or to some other part of the apparatus for treating the plasma for further use. The other outlet of the three-way valve is connected to a treatment means, such as a sorbent cartridge 21, the outlet of which is in turn connected to a particle filter 22 and through the particle filter to the bubble trap 15.

This arrangement can be modified. For example, the plasma reservoir 18 can be incorporated into the plasma filter 13. The reservoir need not be vented, in which case the pumping speed of the plasma pump 19 can be regulated to regulate the plasma reservoir pressure and therefore also the transmembrane pressure across the filter element or filter means of the plasma filter 13.

The various parts of the apparatus are mostly conventional, such as the blood pump, the plasma reservoir, the plasma pump, the sorbent cartridge, the particle filter and the bubble traps. The plasma filter can be any one of a plurality of known types of filters. The filter has membranes of a material which is not affected by whole blood or any of the materials contained therein and which is thus suitable for filtration of plasma from blood. A number of materials are available for use as such membranes, such as hydrophilic materials such as cellulose acetate, cuprophane or cellophane as disclosed in U.S. Pat. No. 4,031,010 to Nose, or polycarbonate or polypropylene, but the preferred materials are polycarbonate such as Nuclepore 040 sold by Nuclepore Corp., and cellulose acetate. The pore size should be from 0.1 to 0.6 microns. The arrangement of the membranes in the filter can be any arrangement suitable for producing a pressure differential across the membrane which causes the plasma to be filtered out as the whole blood flows across the surface of the membrane. A number of other such arrangements can be found in the art. These can be generally divided into parallel film type membrane arrangements, such as shown in the Nose Patent, and hollow fiber arrangements. In the parallel plate arrangements, the space on one side of the parallel plate membranes is connected to the blood inlet and outlet of the filter and the space on the other side of the membrane is connected to the filtrate outlet of the filter. In the hollow fiber arrangements, the fibers are mounted in the filter so that the space within the fiber is connected between the blood inlet and outlet of the filter and the space around the fiber is connected to the filtrate outlet, or vice versa, although the preferred embodiment is with blood flow through the interior of the fiber. The hollow fibers which are particularly suitable are cellulose acetate hollow fibers sold by Asahi Medical Co., Tokyo, Japan. The advantages of this type of membrane over the plate type are that the hollow fiber geometry is inherently strong enough so that no dimensional change occurs at transmembrane pressure necessary to obtain required plasma flows, that due to this structural strength, no additional support structure is necessary, and that because no support structure is necessary, the overall filter structure is simpler and less costly. This is particularly important in light of the strong influence fluid dynamic conditions play upon filtration rate and sieving properties.

Where the apparatus is to be used simply to collect plasma, the three-way valve 20 is turned so that the plasma from the plasma reservoir is discharged to some conventional plasma collection means. Where the apparatus is to be used to treat the separated plasma and return it immediately to the patient, the three-way valve 20 is turned so that the plasma from the reservoir is directed through the treatment, e.g. absorption cartridge 21 to the particle filter 22 and bubble trap 15, whereafter having been filtered to remove any of the treatment particles, the plasma is recombined with the whole blood from line 14.

Where the apparatus is to be used for treating the separated plasma, the sorbent in the cartridge 21 can be any sorbent which is effective for removing the unwanted material from the plasma. U.S. Pat. No. 4,013,564 to Nose suggests several types of sorbents.

It has been found that with the apparatus as described above, by operating it under certain conditions of blood flow and transmembrane pressure, a plasma filtration rate for separating plasma from normal blood which is unexpectedly high can be obtained and also sieving coefficients can be increased. The blood flow rate through the filter should be such that the flow velocity of the blood across the one face of the membrane is from 5 to 1500$^{cm}$/min. The inlet blood pump 10 and the size of the filter should be such that, under the downstream pressure conditions due to directing the blood back to the patient, and the pressure conditions on the plasma side of the filter element or filter means is such, i.e. either atmospheric as in a so-called open system, or a pressure controlled such as by the pump 19, as to be below the pressure on the blood side of the filter, the transmembrane pressure is a positive pressure up to just below 50 mm Hg., and particularly from about 8.5 mm Hg. to just below 50 mm Hg. Preferably the system is operated so that the pressure range is from 40 to 20 mm Hg. When this is done, the plasma filtration rate, i.e. the rate at which plasma is filtered out of the blood through the membrane, is a maximum. By positive transmembrane pressure is meant a transmembrane pressure which is the difference between a higher pressure on the whole blood side of the filter and a lower pressure on the plasma side of the filter.

In order to demonstrate the improved plasma filtration rate, experiments were carried out on dogs, the blood of which was sufficiently similar to whole blood with a substantially normal protein content to provide a useful indication of how the method and apparatus will operate with humans. In each experiment the blood was extracted from the dogs and passed through the system as shown in FIG. 1 under conditions within the ranges set forth above. The pressure on the plasma side of the filter element was atmospheric so that the apparatus is considered to be a so-called open system.

Three normal dogs were perfused a total of seven times, three times using an N type plasma filter, and four times using an S type filter for the filter 13 of FIG. 1.

The two types of filters were both hollow fiber cellulose acetate type filters and corresponded to those from Asahi Medical Co., Tokyo, Japan, under the trademark PLASMAFLO, the fibers having an inside diameter of 370 μm, a wall thickness of 190 μm a porosity of 84% and a nominal pore size of 0.2 μm, the N type filter having 2500 fibers with an effective fiber length (potting to potting in the fiber structure) of 240 mm, and a surface area of about 0.7 m$^2$, and the S type filter having 3300 fibers with an effective fiber length of 200 mm and a surface area of about 0.75 m$^2$. The blood tubing used to supply the blood from the dogs to the filter apparatus and to connect the parts of the filter apparatus with each other was tubing sold under the trademark Lifemed by Lifemed Division of Vernitron, Compton, Calif. The priming volume of the apparatus was about 400 ml. Blood access was via the femoral or internal carotid artery and blood was reinfused via the femoral or jugular vein through FC-100 cannulae sold by Extracorporeal Medical Co., Inc., King of Prussia, Pa. Systemic heparinization was used in each perfusion, 2 mg/kg heparin (A. H. Robins, Richmond, Va.) being injected prior to starting perfusion and 0.5 mg/kg/hr for the rest of the perfusion.

An inlet blood flow of 100 ml/min was maintained by the pump 10, which was a low amplitude pulsatile flow roller pump sold by Drake-Willcock Co., Ltd. which was sufficient to cause a velocity of flow across the membrane of about 25–40$^{cm}$/min. The rate of plasma filtration, the inlet and outlet pressures of the filter and the sorbent cartridge were determined for each perfusion. The transmembrane pressures and flow rates were as shown plotted in FIG. 2.

Contrary to the situation normally encountered when filtering a liquid material through a filter in which the flow of filtered liquid across the filter falls with a drop in transmembrane pressure, it will be seen from FIG. 2. that the amount of plasma which is filtered through the membrane actually increases below pressures heretofore considered a minimum satisfactory transmembrane pressure for filtering plasma, reach a peak at about 30 mm Hg. of transmembrane pressure before falling off. From this Figure it can be seen that the most advantageous transmembrane pressures for achieving the maximum filtration of plasma from normal whole blood lie in the range of from just below 50 mm Hg. to about 8.5 mm Hg. with the best pressures in the range of from about 40 to about 20 mm Hg.

While the data point at the lowest transmembrane pressure shows a plasma flow rate near the maximum, the transmembrane pressure of 8.5 mm Hg. for this point is not a precise pressure for this flow rate. The pressures below 10 mm Hg. cannot be known with any great accuracy because of the utilization of the low amplitude pulsatile flow roller pump and the nature and accuracy of interpretation of the instruments used for the various measurements. The pump does not, as its name makes clear, operate at a steady pressure. It had an amplitude of pressure from the lowest pressure to the highest on the order of 10 mm Hg., which is conventional for plasma separation from blood, and the transmembrane pressures for the respective data points were calculated using the mean value of the pump pressure. Thus the lower pump pressure and thus the transmembrane pressure is somewhat lower than the mean value, possibly as low as about 3.5 mm Hg. Moreover, the pressure gauges used had an accuracy of ±2 mm Hg. at best. Further, the fluid level at the pressure monitoring points was fluctuating, and the column heights of mercury were varying during the pressure readings. For the higher transmembrane pressures, these factors are not very significant, but for those from 10 mm Hg. down, this is very significant. All of these factors together indicate that the transmembrane pressure can be a positive transmembrane pressure near zero and still produce a very high plasma flow as compared to what might normally be expected. The pressures at which the present method is operable is therefore a positive transmembrane pressure up to just below 50 mm Hg. Moreover, due to these factors, the numerical value of 8.5 mm Hg. for the transmembrane pressure for the plasma flow data point at the lowest transmembrane pressure is only approximate, and in fact may be considerably lower. For this reason, the numerical limit on the transmembrane pressure as set forth in the specification and claims is expressed as "about" 8.5 mm Hg., and this expression is intended to include somewhat lower pressures due to the factors discussed hereinabove.

What is claimed is:

1. An apparatus for carrying out separation of plasma from whole blood, comprising:
   a filtration membrane means of a material suitable for separating plasma from whole blood and having a whole blood face and a filtrate face on opposite sides thereof and a pore size from 0.1 to 0.6 microns and having an inlet and an outlet on opposite ends of the whole blood face thereof;
   a bubble trap connected to the inlet of said membrane means;
   a first pump means adapted to be connected to a patient and having the discharge end connected to said bubble trap for directing blood from a patient through said bubble trap and across said whole blood face of said membrane means at a flow velocity of from 5 to 1500 cm/min and at a depth sufficient for enabling separation of plasma from the blood;
   a plasma conduit means having the upstream end connected to the filtrate face of said membrane means for receiving plasma from said membrane means;
   a plasma reservoir included in said conduit means and having a volume substantially larger than the remainder of said conduit means for collecting plasma;
   a second pump means having the intake end connected to the downstream end of said plasma conduit means for applying reduced pressure to the filtrate face of said membrane means through said plasma reservoir for generating a positive pressure differential across said membrane means up to just below 50 mm Hg for forcing the plasma through the membrane;
   a three-way valve;
   a first line connected between the discharge end of said second pump means and said three way valve;
   a second line connected to the outlet for said whole blood face of said membrane means and adapted to be connected to the patient;
   a third line extending from said three-way valve and having a further bubble trap therein and having the end remote from said three-way valve connected to said second line downstream of said membrane means; and
   a fourth line extending from said three way valve for discharging plasma therethrough;
   whereby the path through which the plasma is circulated can be kept short so as to minimize the amount of heat of the blood coming from the patient which will be lost during flow of the blood and plasma through the apparatus and to minimize any adverse changes in the nature of the blood and plasma and the formation of undesirable side products due to the flow of the blood and plasma through the apparatus.

2. An apparatus as claimed in claim 1 in which said membrane means is a film type membrane.

3. An apparatus as claimed in claim 1 in which said membrane means is a hollow fiber membrane.

4. An apparatus as claimed in claim 1 in which said membrane means is a hollow fiber membrane of hydrophilic material.

5. An apparatus as claimed in claim 1 in which said second pump means comprises means for applying a reduced pressure sufficient for generating a pressure differential across said membrane in a range of from about 20 mm Hg to about 40 mm Hg.

6. An apparatus for carrying out separation of plasma from whole blood, comprising:
   a filtration membrane means of a material suitable for separating plasma from whole blood and having a whole blood face and a filtrate face on opposite sides thereof and a pore size from 0.1 to 0.6 microns and having an inlet and an outlet on opposite ends of the whole blood face thereof;
   a bubble trap connected to the inlet end of said membrane means;
   a first pump means adapted to be connected to a patient and having the discharge end connected to said bubble trap for directing blood from a patient through said bubble trap and across said whole blood face of said membrane means at a flow velocity of from 5 to 1500 cm/min and at a depth sufficient for enabling separation of plasma from the blood;
   a plasma conduit means having the upstream and connected to the filtrate face of said membrane means for receiving plasma from said membrane means;
   a plasma reservoir included in said conduit means and having a volume substantially larger than the remainder of said conduit means for collecting plasma;
   a second pump means having the intake end connected to the downstream end of said plasma conduit means for applying reduced pressure to the filtrate face of said membrane means through said plasma reservoir for generating a positive pressure differential across said membrane means up to just below 50 mm Hg for forcing the plasma through the membrane;
   a three-way valve;
   a first line connected between the discharge end of said second pump means to said three way valve;
   a second line connected to the outlet for said whole blood face of said membrane means and adapted to be connected to the patient;
   a third line extending from said three-way valve and having a further bubble trap therein and having the end remote from said three-way valve connected to said second line downstream of said membrane means;
   a blood treatment means having a particle filter therein connected in said third line between said three-way valve and the point at which said third line joines said second line for removing unwanted material from the plasma; and
   a fourth line extending from said three way valve for discharging plasma therethrough;
   whereby the path through which the plasma is circulated can be kept short so as to minimize the amount of heat of the blood coming from the patient which will be lost during flow of the blood and plasma through the apparatus and to minimize any adverse changes in the nature of the blood and plasma and the formation of undesirable side products due to the flow of the blood and plasma through the apparatus.

7. An apparatus as claimed in claim 6 in which said membrane is a film type membrane.

8. An apparatus as claimed in claim 6 in which said membrane means is a hollow fiber membrane.

9. An apparatus as claimed in claim 6 in which said membrane means is a hollow fiber membrane of hydrophilic material.

10. An apparatus as claimed in claim 6 in which said blood treatment means is a sorbent cartridge means.

* * * * *

UNITED STATES PATENT AND TRADEMARK OFFICE
CERTIFICATE OF CORRECTION

PATENT NO. : 4,619,639

DATED : October 28, 1986

INVENTOR(S) : Yukihiko NOSE et al.

It is certified that error appears in the above-identified patent and that said Letters Patent is hereby corrected as shown below:

In the Heading:

[73] Assignee Takeda Chemical Industries, Ltd., Osaka, Japan, and Asahi Medical Co., Ltd., Tokyo, Japan.

Signed and Sealed this

Twenty-seventh Day of October, 1987

Attest:

DONALD J. QUIGG

Attesting Officer

Commissioner of Patents and Trademarks